(12) United States Patent
Chitre et al.

(10) Patent No.: US 7,379,776 B1
(45) Date of Patent: May 27, 2008

(54) STYLET DESIGN

(75) Inventors: Yougandh Chitre, Valencia, CA (US); Gaelle Flammang-Dorie, Brussels (BE)

(73) Assignee: Pacesetter, Inc., Sylmar, CA (US)

( * ) Notice: Subject to any disclaimer, the term of this patent is extended or adjusted under 35 U.S.C. 154(b) by 618 days.

(21) Appl. No.: 11/125,540

(22) Filed: May 9, 2005

(51) Int. Cl.
*A61N 1/05* (2006.01)
*A61M 25/01* (2006.01)
*A61B 5/00* (2006.01)

(52) U.S. Cl. .................. 607/122; 604/19; 604/528; 606/108; 606/129; 600/124; 600/585; 607/119

(58) Field of Classification Search ........... 607/119, 607/63, 115, 122, 116; 604/19, 170, 528, 604/523; 606/41, 108, 12; 600/124, 585
See application file for complete search history.

(56) References Cited

U.S. PATENT DOCUMENTS

| | | | | |
|---|---|---|---|---|
| 4,498,482 | A | 2/1985 | Williams | 128/786 |
| 4,624,266 | A * | 11/1986 | Kane | 607/127 |
| 4,796,642 | A | 1/1989 | Harris | 128/772 |
| 5,728,148 | A | 3/1998 | Boström et al. | 607/116 |
| 5,807,339 | A | 9/1998 | Boström et al. | 604/164 |
| 6,102,887 | A * | 8/2000 | Altman | 604/22 |
| 6,623,480 | B1 | 9/2003 | Kuo et al. | 606/41 |
| 6,887,229 | B1 * | 5/2005 | Kurth | 604/525 |
| 2002/0077583 | A1 | 6/2002 | Clemens et al. | 604/19 |
| 2002/0165536 | A1 | 11/2002 | Kelley et al. | 606/41 |
| 2002/0173785 | A1 | 11/2002 | Spear et al. | 606/41 |

FOREIGN PATENT DOCUMENTS

| | | |
|---|---|---|
| WO | WO 02/49713 A2 | 6/2002 |
| WO | WO 02/49713 A3 | 6/2002 |
| WO | WO 03/090833 A1 | 11/2003 |

* cited by examiner

*Primary Examiner*—Carl H. Layno
*Assistant Examiner*—Natasha Patel

(57) ABSTRACT

A stylet unit is provided for implanting in a body, with the aid of an earlier installed tubular delivery sheath having a lumen with an inner diameter, a lead system including a distal electrode for an implantable cardiac stimulation device being slidably received in the lumen of the introducer device. An elongated main member is engageable with a thrusting region of the lead for advancing the distal electrode to a desired body stimulation site and an integral resilient knob at a proximal end serves to manipulate the main member. The knob has a nominal outer dimension greater than the inner diameter of the delivery sheath lumen and is compressible in directions transverse of the longitudinal axis. The delivery sheath can be slidably advanced across the knob which becomes compressed, enabling its continued slidable transit across the knob and, eventually, free of the lead system and of the stylet unit.

20 Claims, 6 Drawing Sheets

STYLET DESIGN

FIELD OF THE INVENTION

The present invention relates generally to a stylet unit for implanting in a body, with the aid of an earlier installed tubular delivery sheath, a lead system including a distal electrode for an implantable cardiac stimulation device and, more particularly, to a stylet unit which enables the easy prior removal of the delivery sheath and its associated valve and also enables mapping measurements to be obtained to determine optimal electrical characteristics at a desired stimulation site.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bi-directional pulse transmission link between the pacemaker and the heart or may be used to deliver defibrillation shocks to the patient. A typical transvenous type pacing/sensing lead, that is, a lead which is inserted into a vein and guided therethrough into a cavity of the heart, includes at its distal end an electrode designed to contact the endocardium, the tissue lining the inside of the heart. The lead further includes a proximal end having a connector terminal pin adapted to be received by a mating socket in the pacemaker. A flexible, coiled or cabled conductor surrounded by an insulating tube or sheath typically couples the connector terminal pin at the proximal end and the electrode at the distal end.

The implantable cardiac stimulation leads with which the present invention is concerned may take the form of pacemaker leads capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator, commonly known as a "pacemaker" or "pacer", uses one, two, or more flexible leads having one end connected to the pacer and the other end connected to electrodes placed in close proximity to the heart. These leads are used to stimulate or pace the heart. These leads are also used to sense the heart's electrical activity by sensing the heart's signals from their electrodes.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer case or housing. The case, in turn, makes contact with the body tissue and/or fluids. Then the current flows from the pacemaker through the lead's conductor, then through the lead's electrode, then through tissue, and finally to the pacer case.

An alternative solution to using a unipolar lead in a given heart chamber is to use a double lead/electrode in the heart chamber, known as a bipolar lead. In a typical bipolar lead, a second conductor coil or cable is spiraled over or positioned in a separate lumen and insulated from a first conductor along the length of the lead. At the distal end of the lead, one of the conductor cables or coils (inner) is connected to a first electrode, referred to as the "tip" electrode, and the second (outer) conductor coil is connected to a second electrode, referred to as a "ring" electrode. The ring electrode is generally situated about 10 to 20 mm from the tip electrode. The tip electrode is typically placed in contact with heart tissue, while the ring electrode is likely to be mostly in electrical contact with the blood. Because both body tissue and fluids are conductive, the ring electrode of a bipolar lead, in contact with the body fluids, serves as an electrical return for both pacing and sensing.

As earlier noted, the present invention has application to placing leads whose electrodes are either endocardial usage or epicardial usage. In the customary manner, a transvenous lead with an endocardial electrode provides an electrical pathway between the pacemaker, connected to the proximal end of the lead, and endocardial tissue in contact with the distal end of the lead. Endocardial tissue refers to a specific layer of tissue in the interior of the heart's chambers. In such a manner electrical pulses emitted by the pacemaker travel through the endocardial lead and stimulate the heart.

Transveous leads with endocardial electrodes are often placed in contact with the endocardial tissue by passage through a venous access, such as the cephalic or subclavian veins or one of their tributaries. In such a manner transvenous leads offer as an advantage that their electrodes may be placed into contact with the heart without requiring major thoracic surgery. Rather, transvenous leads may be introduced into a vein and maneuvered therefrom so that their electrodes make contact with the endocardium of the heart.

A multi-step procedure is often used to introduce such leads within the venous system. Generally this procedure consists of inserting a hollow needle into a blood vessel, such as the subclavian vein. A wire guide is then passed through the needle into the interior portion of the vessel. The needle is then withdrawn and a delivery sheath and dilator assembly is then inserted over the wire guide into the vessel. The assembly is advanced into a suitable position within the vessel, i.e. so that the distal end is well within the vessel but the proximal end is outside the patient. Next, generally, the dilator and wire guide are both removed, although sometimes the wire guide is retained in place, in case it is needed again. The delivery sheath is left in position and through its hollow lumen offers direct access from outside the patient to the interior of the blood vessel. The ultimate positioning of the lead is often performed with the aid of a stylet unit. The stylet unit has an elongated main member and in its known configuration has a rigid knob at its proximal end for manipulating an enlarged distal tip end engageable with a thrusting region of the lead. In such a fashion a transvenous lead can be easily passed into the vessel through the delivery sheath and ultimately be positioned within the heart. Finally the delivery sheath is removed from the body. With respect to pacemaker leads, however, which typically have a relatively bulky connector pin assembly at the proximal end, the delivery sheath is removed from the body by being split or slit apart. In such a manner the delivery sheath does not have to be large enough to be removed over the relatively bulky connector pin assembly at the proximal end of the lead.

There is an added problem, however, in that the proximal end of the sheath has an integral valve with a lumen and a bore dimensioned smaller than the knob of the stylet unit. The present invention addresses this situation. Typical of the known prior art are U.S. Pat. No. 4,498,482 to Williams, and U.S. Pat. Nos. 5,728,148 and 5,807,339 to Boström et al. which disclose stylet constructions with a ball at the distal end. U.S. Pat. No. 4,796,642 to Harris discloses a stylet with a distal region which includes, successively, a decreasing taper, a flat, an increasing taper, and a tip. U.S. Pat. No. 6,623,480 to Kuo et al. discloses an electrode catheter with a body constructed of PTFE and is electrically conductive. U.S. Patent Application Publication 2002/0077583 to Clemens et al. a catheter with a stylet lumen that collapses upon removal of the stylet. U.S. Patent Application Publications US 2002/0165536 to Kelley et al. and US 2002/0173785 to Spear et al disclose implantable systems in which the delivery sheath and rotatable hemostatic valves are splittable for removal around a manipulating knob.

It was in light of the foregoing that the present invention was conceived and has now been reduced to practice.

SUMMARY

A stylet unit is provided for implanting in a body, with the aid of an earlier installed tubular delivery sheath having a lumen with an inner diameter, a lead system including a distal electrode for an implantable cardiac stimulation device being slidably received in the lumen of the introducer device. An elongated main member is engageable with a thrusting region of the lead for advancing the distal electrode to a desired body stimulation site and an integral resilient knob at a proximal end serves to manipulate the main member. The knob has a nominal outer dimension greater than the inner diameter of the delivery sheath lumen and is compressible in directions transverse of the longitudinal axis. The delivery sheath can be slidably advanced across the knob which becomes compressed, enabling its continued slidable transit across the knob and, eventually, free of the lead system and of the stylet unit.

With the onset of multi chamber pacing for congestive heart failure (CHF), there has been much discussion and debate in the medical community as to what is the most desirable lead possible for left ventricular (LV) stimulation. As a result of recent advancements in techniques and instrumentation, many physicians are convinced that leads as well as accessories, to abet in the implant procedure, are equally important. The overwhelming opinion of physicians seems to be that the "best" LV lead is the one that is easiest to place and involving the fewest implant procedural steps and components. In a known procedure for the implant of a LV lead, for example, the procedural steps entailed include (1) inserting a delivery sheath, (2) inserting the lead to be implanted into the delivery sheath, (3) inserting the stylet, (4) peeling the sheath away from the lead, (5) moving the stylet back to an inactive position, (6) removing part of the valve accompanying the sheath, (7) withdrawing the stylet, and (8) removing the remainder of the valve accompanying the sheath, (9) reinserting the stylet to wedge the lead in place, and (10) withdrawing the stylet.

The present invention teaches the concept and specific design of a stylet that utilizes a compressible knob member for compatibility with a delivery sheath that employs a valve. This novel design represents a significant reduction in the number of implant steps which are as follows: (1) inserting a delivery sheath, (2) inserting the lead to be implanted into the delivery sheath, (3) inserting the stylet, (4) peeling the sheath away from the lead and removing the valve over the stylet knob, (5) using the stylet to wedge the lead in place, and (6) withdrawing the stylet.

In one embodiment of this invention, the stylet knob is composed of a "compressible material". This material could be from a family of polymers, for example. By virtue of the design of the "compressible material", the valve of the sheath can be removed over the stylet knob in a single process. Current stylet knobs are typically composed of a hard plastic requiring a two-step removal process of the valve, namely steps 6 and 8 as noted above, while additionally making the lead susceptible to microdislodgment during steps 5 and 7.

In another embodiment, the stylet may be composed of stainless steel, or equivalent material, and accommodate a welded ball at the distal end so as to mitigate incidences of perforation.

In yet another embodiment, the "compressible material" may serve as a matrix for metallic particles so as to constitute a conductive material. In the alternative, the compressible material may be coated with a conductive material. The length of the stylet could accommodate an insulative coating of PTFE or equivalent material. In this instance, unipolar mapping measurements to determine optimal electrical characteristics at a given implant site can be ascertained by (1) suitable connection between the conductive stylet knob and a PSA, and (2) having the welded ball at the distal end of the stylet in direct or indirect electrical continuity with the cathodal tip electrode.

A primary feature, then, of the present invention is the provision of a stylet unit for implanting in a body, with the aid of an earlier installed tubular delivery sheath, a lead system including a distal electrode for an implantable cardiac stimulation device and enables the easy prior removal of the delivery sheath and its associated valve.

Another feature of the present invention is the provision of such a stylet unit with a manipulating knob at a proximal end which is compressible in directions transverse of its longitudinal axis.

Still another feature of the present invention is the provision of such a stylet unit with a knob member which is compressible in directions transverse of its longitudinal axis and also enables mapping measurements to be obtained to determine optimal electrical characteristics at a desired stimulation site.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
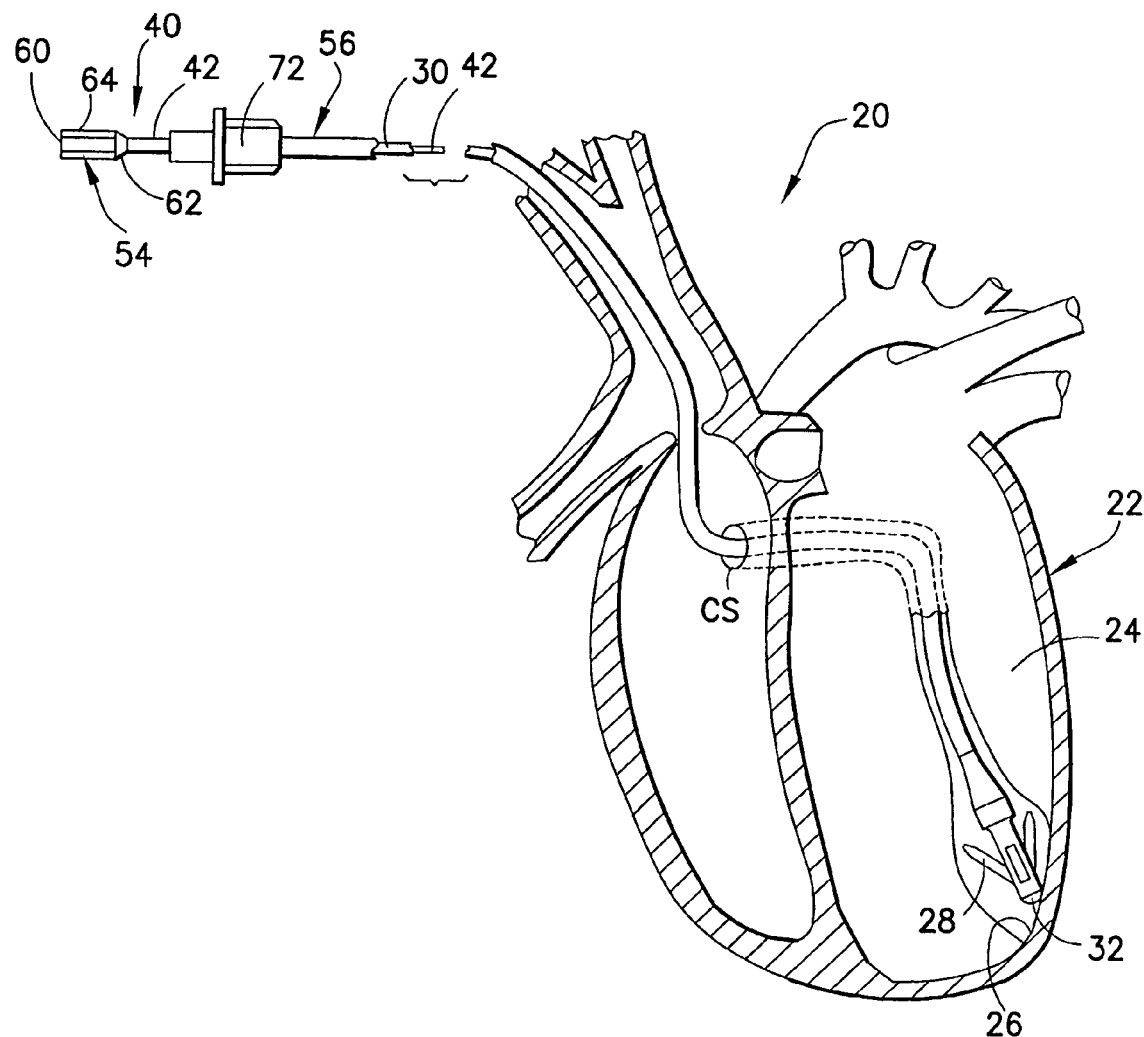
FIG. 1 is a diagrammatic elevation view illustrating a heart with a portion cut away to reveal a known implantable lead assembly, capable of using the invention, secured to a wall of the heart.

Refer now to the drawings and, initially, to FIG. 1 in which is shown a diagrammatic elevation view, partially cut away, of an implanted lead system 20 for providing electrical stimulation of a heart 22 incorporating features of the present invention. In FIG. 1, the lead system 20 is shown extending into the left ventricle 24 via the coronary sinus CS. Although the present invention will be described with reference to the embodiments shown in the drawings, it should be understood that the present invention may be embodied in many alternate forms or embodiments. For example, while the illustrated lead system is of the passive fixation variety, it is within the scope of this invention that it be of the active fixation variety. In addition, any suitable size, shape or type of elements or materials consistent with the invention could be used. In this instance, the lead system 20 is attached to an interior wall 26 of the heart 20 by means of fixing tines 28 which engage the tissue or trabeculae of the heart.

Figure 2:
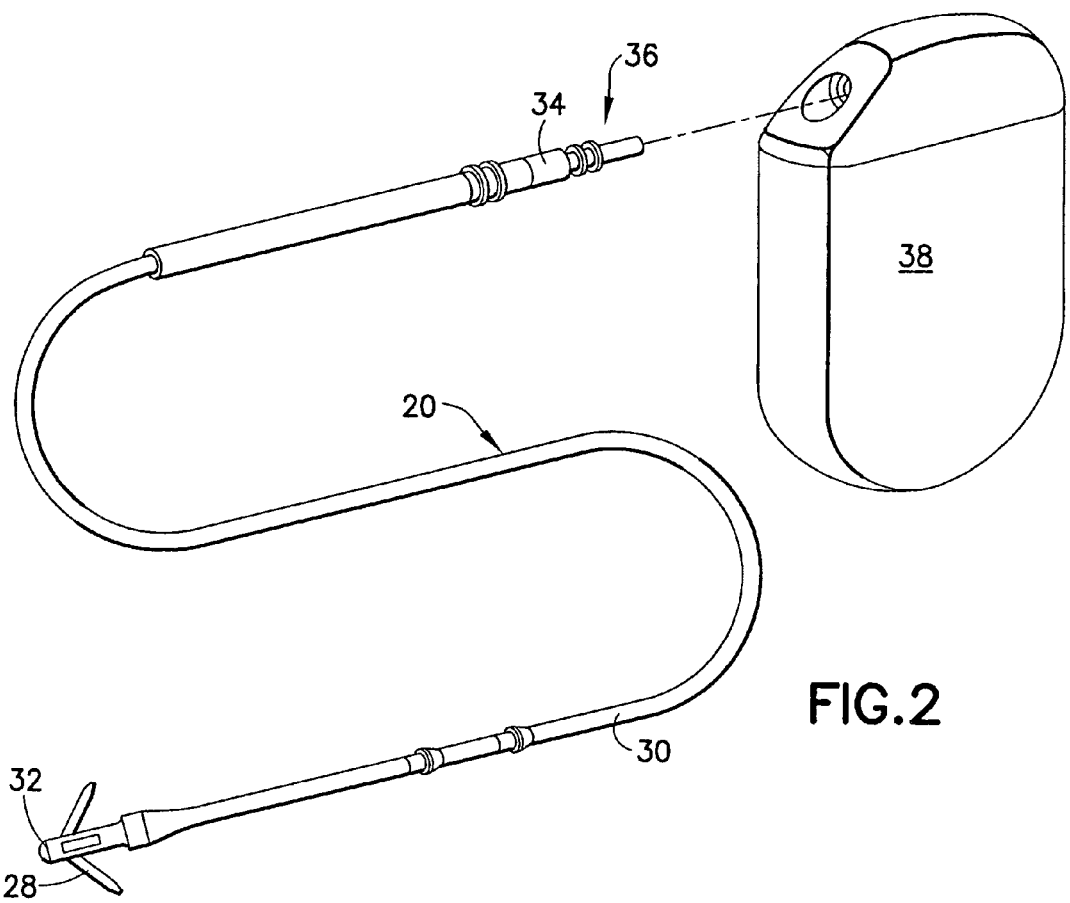
FIG. 2 is a perspective view of a known implantable lead system in combination with a stimulating device such as a pacemaker, the lead system capable of modification to use the invention.
Figure 3:
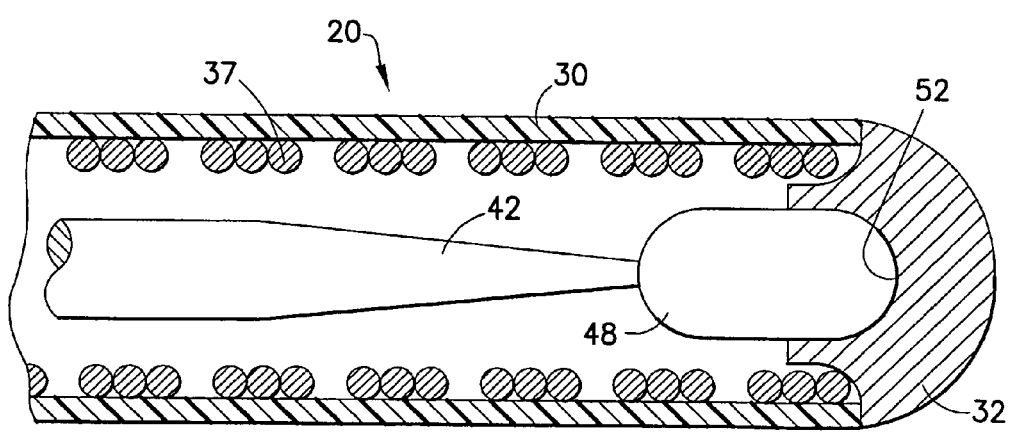
FIG. 3 is a longitudinal cross section view of the combination of distal end of the lead system and stylet unit.

As further illustrated, now viewing FIG. 2 along with FIG. 1, the lead system 20 also includes an insulating sheath 30 interconnecting a distal electrode 32 secured adjacent the interior wall 26 and a proximal electrical connector 34 at a proximal end 36 to which can be attached a source of electrical energy such as a pacemaker 38 (FIG. 2). A conductor 37 (FIG. 3) electrically connects the distal electrode 32 to the electrical connector 34.

In FIG. 1, a stylet unit 40 is illustrated inserted within the insulating sheath 30. A primary function of the stylet unit is to advance the distal electrode 32 to a desired stimulation site in the body and also serves to provide rigidity to the lead system 20 during insertion of the lead system 20 into the heart 22. Viewing especially FIG. 4, the stylet unit 40 includes an elongated main member 42, typically a stainless steel wire, having a longitudinal axis 44 extending between a proximal end 46 and an enlarged element 48 at a distal end 50. The enlarged element 48 is engageable with a thrusting region 52 of the lead for advancing the distal electrode to a desired stimulation site in the body such as indicated at 26 in FIG. 1. A knob or finger grip 54 is suitably provided at a proximal extremity of the stylet unit 40 for its manipulation. The knob 54 is of resilient composition, any biocompatible polymer being a suitable material for purposes of the invention, fixed to the proximal end of the main member for manipulating the main member.

For the implantation process, the stylet unit 40 is preferably used in combination with a delivery sheath 56 (FIGS. 1 and 5) which will have been earlier installed into the heart 22. The delivery sheath has a lumen 58 with an inner diameter sufficiently large to slidably receive the lead system 20. With the delivery sheath 56 advanced to the farthest location possible, the stylet unit is then inserted into the lead system 20 and itself advanced until the enlarged element 48 engages the thrusting region 52 of the distal electrode 32. The knob 54 is generally aligned with the longitudinal axis 44 of the main member 42 and, in its initial state, viewing FIG. 4, has a nominal outer dimension greater than the inner diameter of the lumen 58 of the delivery sheath 56. However, the knob 54 is compressible in directions transverse of the longitudinal axis 44 such that the delivery sheath 56, notwithstanding the fact that the lumen 58 has a smaller transverse or outer dimension than that of the knob, can be slidably removed from the body and from the lead system and from the stylet unit. To this end, the delivery sheath 56 is advanced across the knob which becomes compressed to a reduced outer dimension generally equivalent to the inner diameter of the delivery sheath, enabling the slidable transit of the delivery sheath across the knob and, eventually, free of the lead system 20 and of the stylet unit 40.

Figure 4:
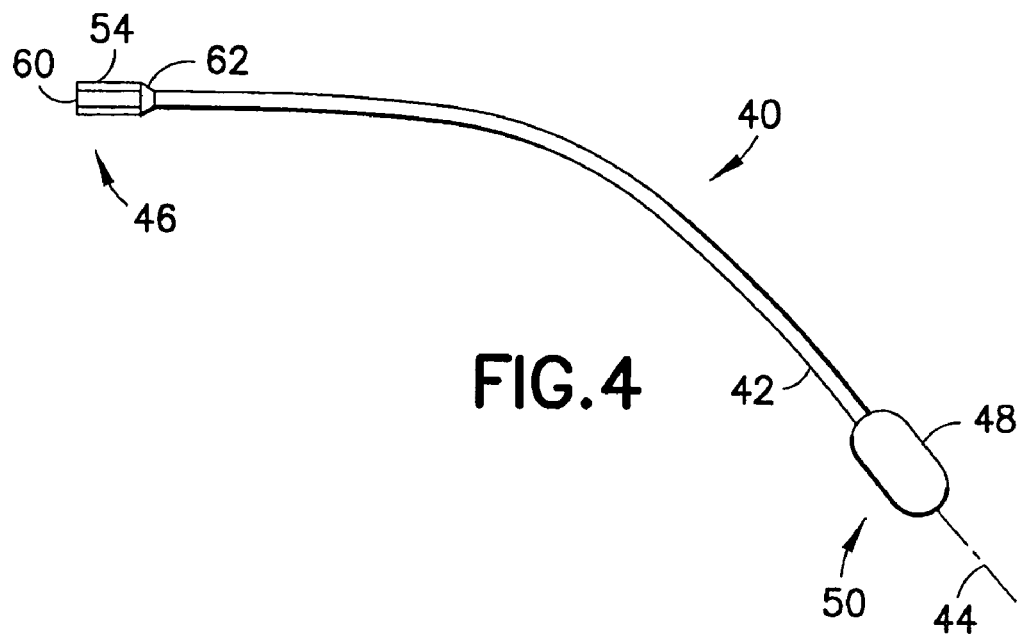
FIG. 4 is an elevation view of a stylet unit embodying the invention.
Figure 5:
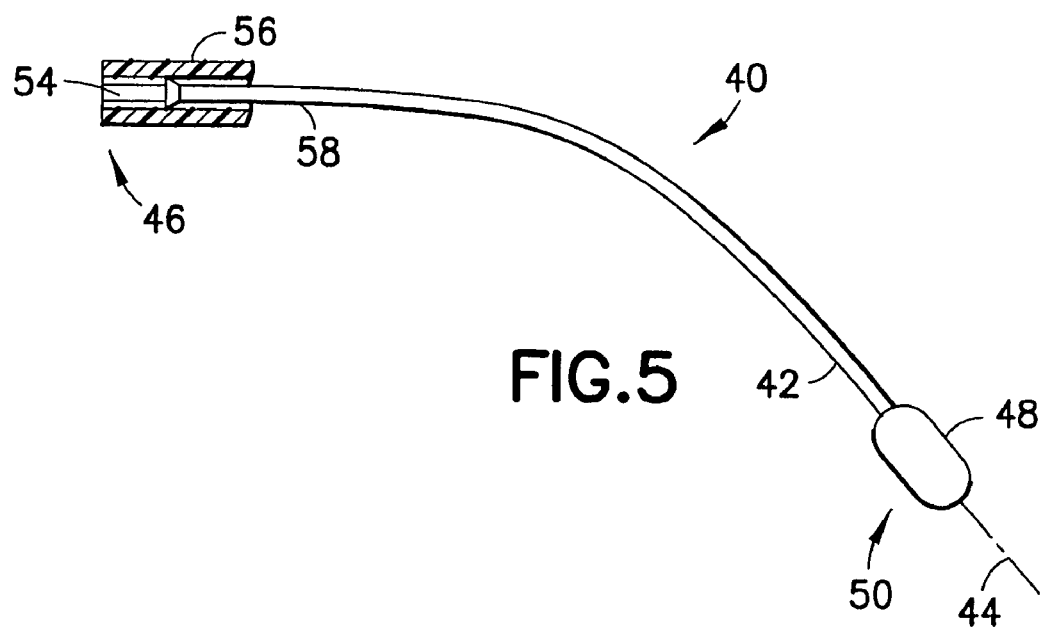
FIG. 5 is an elevation view of the stylet unit of FIG. 4 shown engaged with a small portion of a delivery sheath.
Figure 6:
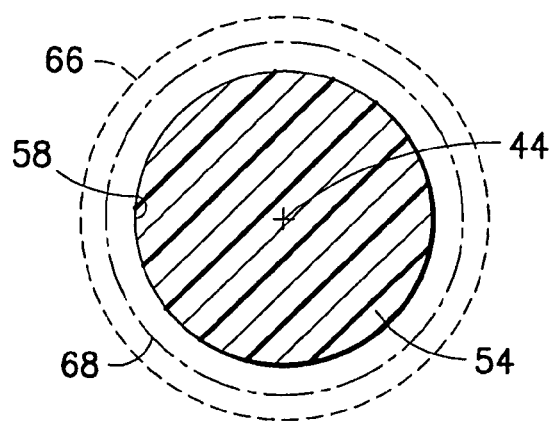
FIG. 6 is a transverse cross section view of a knob of the stylet unit of the invention engaged with a delivery sheath.

As seen especially well in FIGS. 1 and 4, the knob 54 extends between a proximal end 60 and a distal end 62, is coaxial with the main member 42, has an intermediate region 64 of substantially constant or outer dimension, and is tapered at its distal end for ease of reception of the lumen of the delivery sheath 56. In one instance, viewing FIG. 6, the knob 54 is composed of foam material which compresses from its original transverse or outer dimension as indicated by a dashed line 66 toward the longitudinal axis 44, being slidably engaged with the lumen 58 when the delivery sheath 56 slidably transits across the knob. In FIG. 6, line 68 represents the outer peripheral surface of the delivery sheath.

Figure 7:
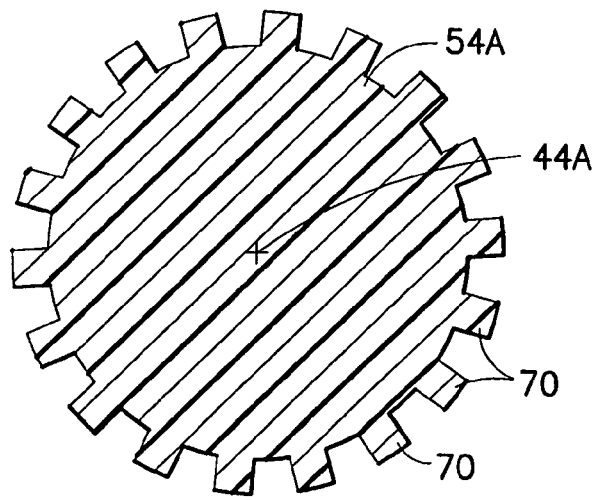
FIG. 7 is a transverse cross section view of another embodiment of the knob of the stylet unit of the invention.
Figure 8:
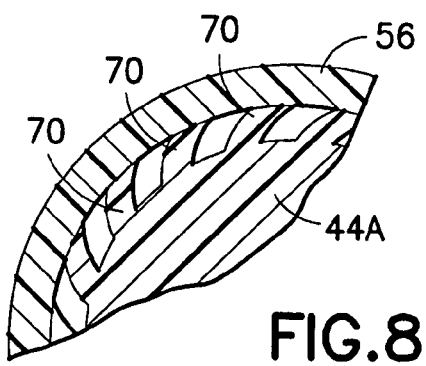
FIG. 8 is a detail cross section view of the embodiment shown in FIG. 7 engaged with a delivery sheath.

In another instance, viewing FIG. 7, a modified knob 54A includes a plurality of fins 70 projecting transversely from a longitudinal axis 44A. Then, viewing FIG. 8, the fins 70 are seen folding circumferentially in the same direction toward one another when the delivery sheath slidably transits across the knob.

A particular benefit of the invention is noticed when the delivery sheath 56 employs a valve 72 as seen in FIG. 1. The valve 72 is fabricated of hardened material and cannot be peeled away in the known manner available for removal of the delivery sheath delivery sheath. However, with a knob having the characteristics just described and the valve 72 having a lumen aligned with and similar sized to the lumen 58 of the delivery sheath delivery sheath 56, the valve itself slidably transits across the knob until it, also, is free of the lead system and of the stylet unit, generally in the manner diagrammatically shown in FIG. 6.

Figure 9:
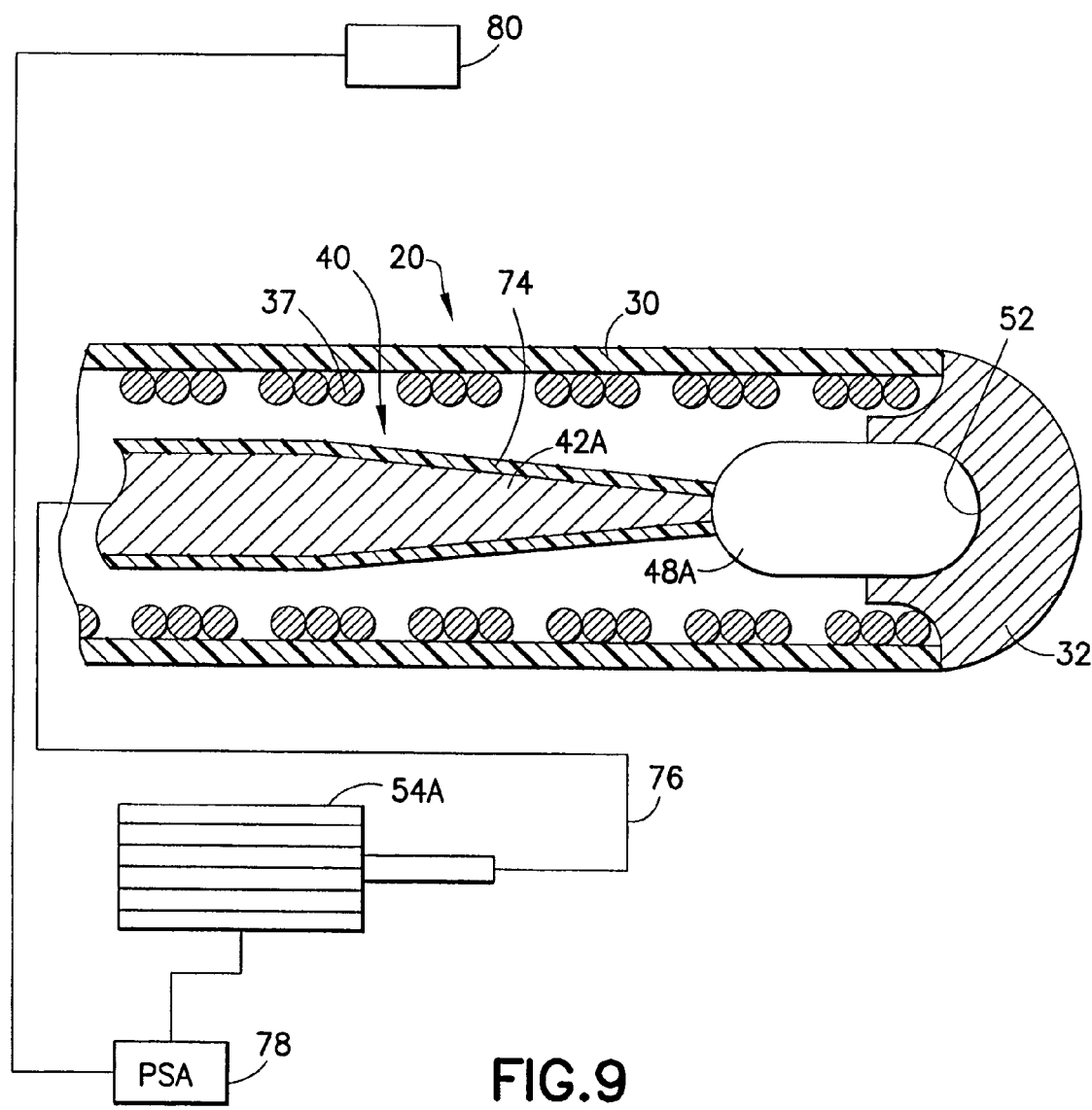
FIG. 9 is a longitudinal cross section view of the combination of distal end of the lead system and a modified stylet unit and another component.

Yet another embodiment is illustrated in FIG. 9. In this instance, a modified stylet unit 40A is employed to advance the distal electrode 32 to a desired stimulation site. The stylet unit includes a main member 42A which is of an electrically conductive metal coated with an insulative material 74 such as PTFE. The composition of a knob 54A includes a matrix of metallic particles in electrical continuity with the main member 42A. An electric conductor 76 connects the knob 54A to a pacing system analyzer (PSA) 78 of known design enabling mapping measurements to be obtained between the electrode 32 and a reference electrode 80 to determine optimal electrical characteristics at a desired stimulation site such as indicated at 26 in FIG. 1. As previously, this occurs when the distal end of the main member 42A is engaged with the thrusting region 52 of the lead and the distal electrode 32 advanced to the desired stimulation site.

Figure 11:
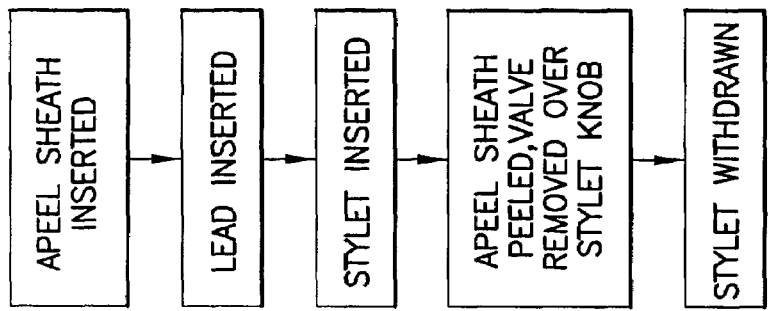
FIG. 11 is a flow chart presenting the steps required for implanting a lead in accordance with the techniques and construction of the invention.
Figure 10:
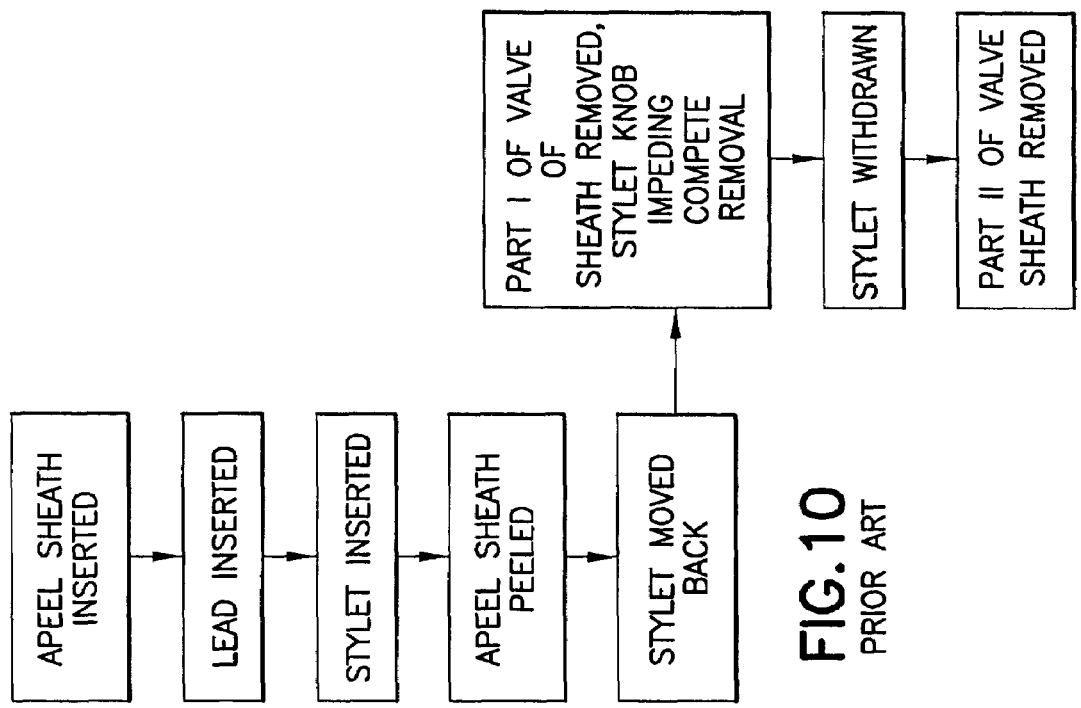
FIG. 10 is a flow chart presenting the steps required for implanting a lead in accordance with known techniques.

With the construction of the invention now complete, it may be helpful to describe the benefits achieved by the invention by way of a pair of flow charts presented as FIGS. 10 and 11. FIG. 10 is a flow chart presenting the steps required for implanting a lead in accordance with known techniques, prior to the invention, and FIG. 11 is a flow chart presenting the steps required for implanting a lead in accordance with the techniques and construction of the invention. The steps of the invention as depicted in FIG. 11 represent a significant reduction of the steps required by the surgeon during an implant procedure.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A stylet unit for implanting in a body, with the aid of an earlier installed tubular delivery sheath having a lumen with an inner diameter, a lead system including a distal electrode for an implantable cardiac stimulation device being slidably received in the lumen of the introducer device, the stylet unit comprising:
    an elongated main member having a longitudinal axis extending between a proximal end and a distal end engageable with a thrusting region of the lead for advancing the distal electrode to a desired stimulation site in the body; and
    a knob of resilient composition fixed to the proximal end of the main member for manipulating the main member, the knob being generally aligned with the longitudinal axis of the main member and having a nominal outer dimension greater than the inner diameter of the lumen of the delivery sheath and being compressible in directions transverse of the longitudinal axis to slidably remove the delivery sheath from the body and from the lead system and from the stylet unit, advancing the delivery sheath across the knob which becomes compressed to a reduced outer dimension generally equivalent to the inner diameter of the delivery sheath enabling its slidable transit across the knob and, eventually, free of the lead system and of the stylet unit.

2. A stylet unit as set forth in claim 1 wherein the knob extends between a proximal end and a distal end and is tapered at its distal end for ease of reception of the lumen of the delivery sheath.

3. A stylet unit as set forth in claim 1 wherein the knob extends between a proximal end and a distal end, includes an intermediate region of substantially constant transverse dimension and is tapered at its distal end for ease of reception of the lumen of the delivery sheath.

4. A stylet unit as set forth in claim 1 wherein the knob is coaxial with the main member and extends between a proximal end and a distal end, includes an intermediate region of substantially constant transverse dimension and is tapered at its distal end for ease of reception of the lumen of the delivery sheath.

5. A stylet unit as set forth in claim 1 wherein the knob includes a plurality of fins projecting transversely from the longitudinal axis, the fins folding circumferentially in the same direction toward one another when the delivery sheath slidably transits across the knob.

6. A stylet unit as set forth in claim 1 wherein the knob is composed of foam material which compresses toward the longitudinal axis when the delivery sheath slidably transits across the knob.

7. A stylet unit as set forth in claim 1 wherein the main member is an electrically conductive metal coated with an insulative material;
    wherein the composition of the knob includes a matrix of metallic particles in electrical continuity with the main member; and
including:
    an electric conductor connecting the knob to a pacing system analyzer enabling mapping measurements to be obtained to determine optimal electrical characteristics at a desired stimulation site when the distal end of the main member is engaged with the thrusting region of the lead and the distal electrode advanced to the desired stimulation site.

8. A stylet unit as set forth in claim 1 wherein the main member is an electrically conductive metal coated with an insulative material;
    wherein the knob is of a compressible biocompatible material coated with a conductive material in electrical continuity with the main member; and
including:
    an electric conductor connecting the knob to a pacing system analyzer enabling mapping measurements to be obtained to determine optimal electrical characteristics at a desired stimulation site when the distal end of the main member is engaged with the thrusting region of the lead and the distal electrode advanced to the desired stimulation site.

9. In combination, a removable implantable cardiac stimulation lead system for use with an implantable stimulation device and an implanting system for directing the lead system to a desired stimulation site in the body, the combination comprising:
    a tubular delivery sheath having a lumen with an inner diameter, the lead system being slidably received in the lumen of the introducer device;
    the lead system including:
    a proximal connector coupled to a distal electrode by a conductor, the conductor being surrounded by an insulating sheath and having an axially extending lumen therein, and a thrusting region proximate the distal electrode; and
    a stylet unit for implanting the lead system including:
    an elongated main member having a longitudinal axis extending between a proximal end and a distal end and engageable with the thrusting region of the lead for advancing the lead to a desired stimulation site in the body; and
    a knob of resilient composition fixed to the proximal end of the main member for manipulating the main member, the knob being generally aligned with the longitudinal axis of the main member and having a nominal outer dimension greater than the inner diameter of the lumen of the delivery sheath and being compressible in directions transverse of the longitudinal axis to slidably remove the delivery sheath from the body and from the lead system and from the stylet unit, advancing the delivery sheath across the knob which becomes compressed to a reduced outer dimension generally equivalent to the inner diameter of the delivery sheath enabling its slidable transit across the knob and, eventually, free of the lead system and of the stylet unit.

10. The combination as set forth in claim 9 wherein the knob extends between a proximal end and a distal end and is tapered at its distal end for ease of reception of the lumen of the delivery sheath.

11. The combination as set forth in claim 9 wherein the knob extends between a proximal end and a distal end, includes an intermediate region of substantially constant outer dimension and is tapered at its distal end for ease of reception of the lumen of the delivery sheath.

12. The combination as set forth in claim 9 wherein the knob is coaxial with the main member and extends between a proximal end and a distal end, includes an intermediate region of substantially constant outer dimension and is tapered at its distal end for ease of reception of the lumen of the delivery sheath.

13. The combination as set forth in claim 9 wherein the knob includes a plurality of fins projecting transversely from the longitudinal axis, the fins folding circumferentially in the same direction onto one another when the delivery sheath slidably transits across the knob.

14. The combination as set forth in claim 9 wherein the knob is composed of flexible resilient foam material and has a longitudinal axis aligned with the main member which compresses toward the longitudinal axis when the delivery sheath slidably transits across the knob.

15. A stylet unit as set forth in claim 9 wherein the main member is an electrically conductive metal coated with an insulative material; wherein the composition of the knob includes a matrix of metallic particles in electrical continuity with the main member; and including:
an electric conductor connecting the knob to a pacing system analyzer enabling mapping measurements to be obtained to determine optimal electrical characteristics at a desired stimulation site when the distal end of the main member is engaged with the thrusting region of the lead and the distal electrode advanced to the desired stimulation site.

16. A method of implanting a lead system for use with an implantable cardiac stimulation device comprising the steps of:
(a) slidably advancing into the body a tubular delivery sheath, extending between proximal and distal ends and having a lumen with an inner diameter, until the distal end thereof is proximate a desired stimulation site;
(b) providing the lead system with a proximal connector coupled to a distal electrode by a conductor, the conductor being surrounded by an insulating sheath, an axially extending lumen therein, and a thrusting region adjacent the distal electrode;
(c) slidably introducing the lead system into the lumen of the delivery sheath;
(d) providing a stylet unit including an elongated main member extending between a proximal end and a distal end engageable with the thrusting region of the lead for advancing the lead to the desired stimulation site in the body and a knob of resilient composition at the proximal end of the main member for manipulating the main member, the knob having a nominal outer dimension greater than the inner diameter of the lumen of the delivery sheath and being compressible in directions transverse of the longitudinal axis; and
(e) slidably removing the delivery sheath from the body and from the lead system and from the stylet unit by withdrawing the delivery sheath across the knob, compressing the knob to a reduced outer dimension generally equivalent to the inner diameter of the delivery sheath enabling its slidable transit across the knob thereby, eventually, becoming free of the lead system and of the stylet unit.

17. A method of implanting a lead system as set forth in claim 16 wherein the knob extends between a proximal end and a distal end and is tapered at its distal end for ease of reception of the lumen of the delivery sheath.

18. A method of implanting a lead system as set forth in claim 16 wherein the knob extends between a proximal end and a distal end, includes an intermediate region of substantially constant outer dimension and is tapered at its distal end for ease of reception of the lumen of the delivery sheath.

19. A method of implanting a lead system as set forth in claim 16 wherein the knob is coaxial with the main member and extends between a proximal end and a distal end, includes an intermediate region of substantially constant outer dimension and is tapered at its distal end for ease of reception of the lumen of the delivery sheath.

20. A method of implanting a lead system as set forth in claim 16 wherein the knob includes a plurality of fins projecting radially from the longitudinal axis, the fins folding circumferentially in the same direction onto one another when the delivery sheath slidably transits across the knob.

* * * * *